United States Patent [19]

Mawatari et al.

[11] 4,214,909
[45] Jul. 29, 1980

[54] AQUATIC ANTIFOULING METHOD

[75] Inventors: Shizuo Mawatari, Tokyo; Takashi Nishida, Kurashiki, both of Japan

[73] Assignee: Kuraray Co., Ltd., Kurashiki, Japan

[21] Appl. No.: 860,723

[22] Filed: Dec. 15, 1977

[30] Foreign Application Priority Data

Dec. 17, 1976 [JP] Japan .................................. 51-152369

[51] Int. Cl.$^2$ ............................................... C09D 5/14
[52] U.S. Cl. ........................................ 106/16; 106/18; 106/18.32; 106/18.35; 424/314
[58] Field of Search ................ 560/249; 568/827, 875; 424/314; 106/15 R, 16, 15.05, 18, 18.32, 18.35

[56] References Cited

U.S. PATENT DOCUMENTS

| | | | |
|---|---|---|---|
| 2,797,235 | 6/1957 | Birbiglia et al. | 560/249 |
| 3,801,652 | 4/1974 | Ruegg et al. | 560/249 |
| 4,006,193 | 2/1977 | Ninagawa et al. | 568/875 |

FOREIGN PATENT DOCUMENTS 51-118830 10/1976 Japan .
51-132223 11/1976 Japan .

*Primary Examiner*—Lorenzo B. Hayes
*Attorney, Agent, or Firm*—Burns, Doane, Swecker & Mathis

[57] ABSTRACT

Method for controlling fouling to structures caused by aquatic fouling organisms such as barnacles, slime, sea moss, algae, etc. which comprises applying to said structures sesquiterpene alcohols such as farnesol, nerolidol, and dehydronerolidol, and the organic carboxylic acid esters thereof.

39 Claims, No Drawings

AQUATIC ANTIFOULING METHOD

BACKGROUND OF THE INVENTION

1. Field of the Invention

The present invention relates to a method and compositions therefor for rendering structures subject to aquatic environments resistant to fouling by aquatic organisms such as barnacles, algae, sea moss, slime, etc. It particularly relates to the control of such organisms through the use of novel antifouling agents.

2. Description of the Prior Art

As used herein, the term "structure subject to aquatic environments" refers broadly to any object which is in contact with an aqueous environment. By way of example, but not of limitation, such structures include all forms of watercraft, including both the moving and static varieties; underwater static structures such as wharfs, piers, pilings, bridge substructures, etc.; underwater machinery such as heat exchangers, water inlet and outlet pipes, pumps, etc.; and such objects as ropes, fishnets, etc. In short, any object which is in contact with a water environment, and upon which the growth of fouling organisms is undesirable may be efficaciously protected through the use of the method and compositions of the instant invention. Currently, in coastal areas large quantities of sea water are utilized by power plants, petrochemical plants, etc. as industrial cooling water. In these installations, the attachment and growth of Hydrozoa, *Hydroides norvegica,* Ostrea, *Mytilus edulis, Balanus amphitrite hawaiensis,* Bryozoa, Ulva, Enteromorpha, Ectocarpus, Ascidiacea, on the waterway heat exchangers and the main and auxiliary water pipes adapted for intake and disposal of waste cooling water result in such undesirable consequences such as the reduction of sea water intake, reduction of cooling efficiency, and the fouling of water pipes. Similarly, the deposit and growth of these fouling organisms on the bottoms and sides of ships and other watercraft causes a reduction in cruising speed, increased fuel costs, and an accelerated corrosion of hull materials. The above-mentioned fouling organisms also attach themselves to fishnets, ropes, etc., regardless of whether they are manufactured of synthetic or natural fiber, gradually plugging the meshes of the nets or increasing the surface area of the ropes, increasing their wave resistance with an attendant debilitive effect on net deployment. The growth of these organisms on fishnets used in fish nurseries, such as yellowtail nurseries, has a particularly deleterious effect, causing a reduction in the supply of nutrients available to the fish, or a sagging or breaking of fishnets due to their increased weight, both of which result in a reduction of fish yield. The underwater structures, rigs, machinery, etc. are also subject to biological degradation of their materials due to the deposit and growth of the above fouling organisms, or are subject to handling inconveniences. Heretofore, chlorine, sodium hypochloride, formalin, etc. have been employed for the prevention of the attachment and growth of such fouling organisms in aquatic structures. However, these substances have been less than satisfactory in that they are not only inadequate in activity against these fouling organisms, but tend to cause pollution and corrosion of equipment. Furthermore, marine paints and underwater antifouling paints containing compounds of tin, mercury, copper, zinc, arsenic, or other metals have been employed by the prior art in an effort to combat the attachment and growth of fouling organisms on ships and other underwater structures. However, these metallic compounds have proved to be unsatisfactory in that they tend to corrode ship-hull materials or to be deactivated by reactions with the hydrogen sulfide present in harbor and port water. It has also been proposed in Japanese Patent Publication No. 34448/1976, Japanese Patent Application Laid-Open No. 118830/1976; and Japanese Patent Application Laid-Open No. 132223/1976 to employ certain geraniol compounds as antifouling agents. However, even these compounds exhibit a still less than desirable activity against the above-mentioned fouling organisms.

Therefore, in the watercraft, harbor, power, chemical, and fish-nursing industries, research has continued for compounds which exhibit a high selective activity against the aforementioned aquatic fouling organisms, which exhibit a low toxicity to human beings and other animals, a low toxicity to fish and edible shell-fish, and which are easy to handle, and have a long duration of activity.

SUMMARY OF THE INVENTION

Accordingly, it is an object of the instant invention to provide an antifoulant agent which exhibits a high activity against aquatic fouling organisms.

It is an additional object of the instant invention to provide an antifoulant agent which is selectively toxic to aquatic fouling organisms and is non-toxic to humans and other animals, and only very low in toxicity to fish and edible shell fish.

A further object of the present invention is the provision of an antifoulant agent which is noncorrosive to metal surfaces.

Yet another object of the instant invention is the provision of an antifoulant agent which has a long duration of activity.

Still another object of the present invention is the provision of antifoulant coatings and compositions with such an antifoulant agent as the active ingredient.

An additional object of the instant invention is the provision of a highly efficacious method for rendering structures exposed to aqueous environments resistant to fouling by aquatic organisms.

In accomplishing the foregoing and other objects, applicants have found that certain sesquiterpene alcohols or the organic carboxylic acid esters thereof are highly efficacious antifoulant agents which exhibit a high selective activity against aquatic fouling organisms, and which also exhibit an outstanding duration of activity. Applicants have found that the deposit and growth of the aforementioned aquatic fouling organisms may be successfully controlled by contact with the sesquiterpene compounds of the instant invention, or mixtures thereof. The advantages of the present invention may be accrued by formulating the sesquiterpene compounds of the instant invention with a compatible carrier and applying this admixture to a structure subject to an aqueous environment, or by compounding the present antifoulant agents into the structure itself. Alternatively, aquatic fouling organisms may be effectively controlled in accordance with the instant invention by dissolving or dispersing the sesquiterpene antifoulant agents in the aqueous environment. Accordingly, the present invention provides antifoulant agents which are highly suited for the control of aquatic fouling organisms.

DETAILED DESCRIPTION OF THE PREFERRED EMBODIMENTS

Applicants have found that sesquiterpene compounds of the general formula (I):

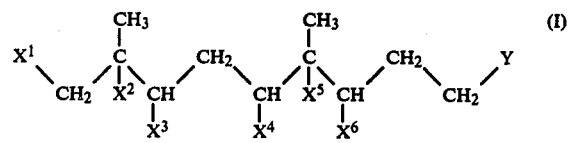

wherein $X^1$, $X^2$, and $X^3$ each is a hydrogen atom, or one of $X^1$ and $X^3$ is a hydrogen atom with the other and $X^2$ representing a double bond in the carbon chain of the compound; $X^4$, $X^5$, and $X^6$ each is a hydrogen atom, or one of $X^4$ and $X^6$ is a hydrogen atom with the other and $X^5$ representing a double bond in the carbon chain of the compound; and Y is a group selected from the group consisting of:

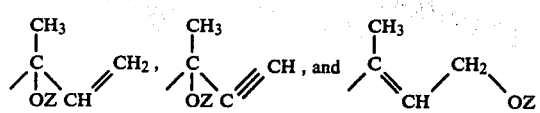

wherein Z is a hydrogen atom or

with R being either a hydrogen atom or a hydrocarbon group which may optionally be substituted, have more potent selective controlling activity against aquatic fouling organisms than prior art antifoulant agents, such as the above-mentioned geraniol compounds, while at the same time are not only low in toxicity to humans and other animals, but also are very low in toxicity to fish and edible shell fish.

Among the foregoing sesquiterpene compounds, applicants have found that particularly efficacious antifouling agents are provided by sesquiterpene compounds of general formulas II, III, and IV:

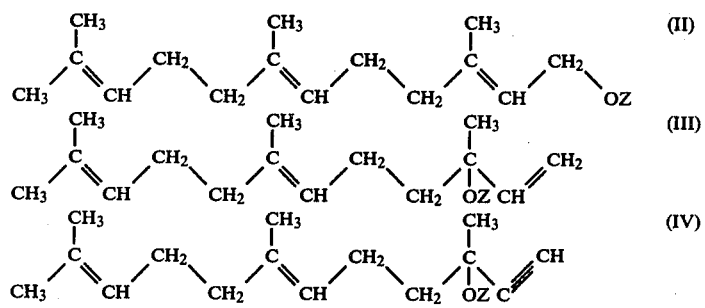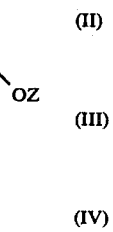

In the above general formulas, the group R may, for example, be a hydrogen atom, an alkyl group containing 1 to 8 carbon atoms, an alkenyl group containing 2 to 8 carbon atoms, an aralkyl group containing 7 to 11 carbon atoms or an aryl group containing 6 to 10 carbon atoms. The aralkyl and aryl groups, in particular, may be nuclearly substituted by substituents such as halogen, alkyl, hydroxy, alkoxy, nitro, amino, dioxy, and other groups. Preferred species of R are lower alkyl groups such as methyl, ethyl, propyl, butyl, pentyl, etc.; lower alkenyl groups such as ethenyl (vinyl), propenyl, butenyl, etc.; aralkyl groups such as benzyl, piperonyl, methylbenzyl, etc.; and aryl groups such as phenyl, hydroxyphenyl, 3,4-methylenedioxyphenyl, chlorophenyl, dichlorophenyl, methylphenyl, methylaminophenyl, methoxyphenyl, nitrophenyl, etc. The nuclear substituents alkyl and alkoxy are preferably lower alkyl and lower alkoxy, and the dioxy moiety is bridged by a lower alkylene radical.

The sesquiterpene compound of the above general formulas I–IV include, for example, farnesol (3,7,11-trimethyl-2,6,10-dodecatrien-1-ol); 3,7,11-trimethyl-2,7,10-dodecatrien-1-ol; 3,7,11-trimethyl-2,6,11-dodecatrien-1-ol; 3,7,11-trimethyl-2-dodecen-1-ol; nerolidol (3,7,11-trimethyl-1,6,10-dodecatrien-3-ol); 3,7,11-trimethyl-1,7,10-dodecatrien-3-ol; 3,7,11-trimethyl-1,6,11-dodecatrien-3-ol; 3,7,11-trimethyl-1,6-dodecadien-3-ol; 3,7,11-trimethyl-1,10-dodecadien-3-ol; 3,7,11-trimethyl-1-dodecen-3-ol; dehydronerolidol (3,7,11-trimethyl-6,10-dodecadien-1-yn-3-ol); 3,7,11-trimethyl-7,11-dodecadien-1-yn-3-ol; 3,7,11-trimethyl-6,11-dodecadien-1-yn-3-ol; 3,7,11-trimethyldodecan-1-yn-3-ol; etc.; as well as any organic carboxylic acid esters of said alcohols. The acid moieties constituting such organic carboxylic acid esters of such alcohols may be saturated hydrocarbon carboxylic acids and saturated fatty acids such as formic acid, acetic acid, propionic acid, butyric acid, valeric acid, pivalic acid, etc.; unsaturated hydrocarbon and fatty acids such as acrylic acid, methacrylic acid, crotonic acid, senecioic acid ($\beta,\beta$-dimethylacrylic acid), etc.; aromatic carboxylic acids such as benzoic acid, p-hydroxybenzoic acid, p-chlorobenzoic acid, 3,4-dichlorobenzoic acid, p-methylbenzoic acid, o-methylaminobenzoic acid, p-methoxybenzoic acid, piperonylic acid, p-nitrobenzoic acid, etc.; and so forth. Among those compounds, farnesol and the organic carboxylic acid esters of farnesol exhibit particularly excellent controlling activity against aquatic fouling organisms.

The sesquiterpene alcohols and carboxylic acid esters, which are the aquatic antifouling agents of the present invention, are known compounds and can be easily produced by conventional methods of synthesis. For example, geranylacetone may be reacted with acetylene to obtain dehydro-nerolidol which may be partially hydrogenated to nerolidol which, in turn, may be converted to farnesol by allylic rearrangement. Other sesquiterpene alcohols may be easily obtained, for example, by the following routes of synthesis.

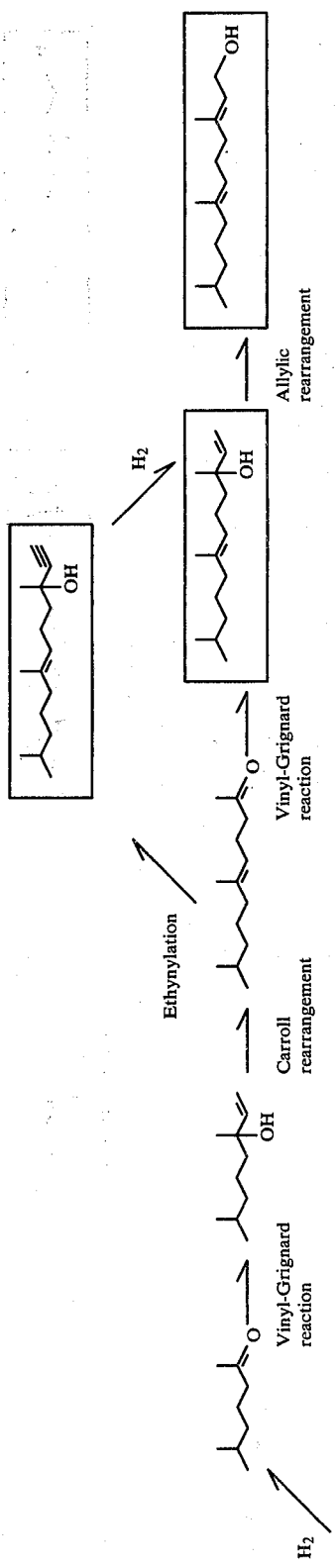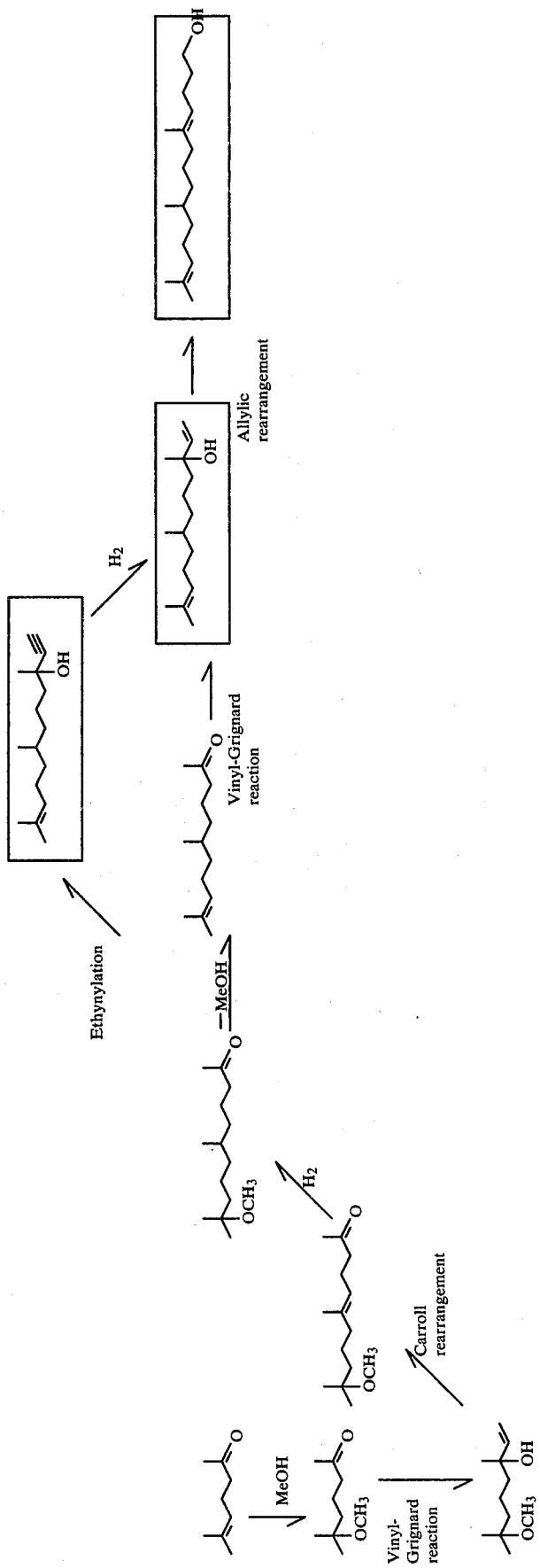

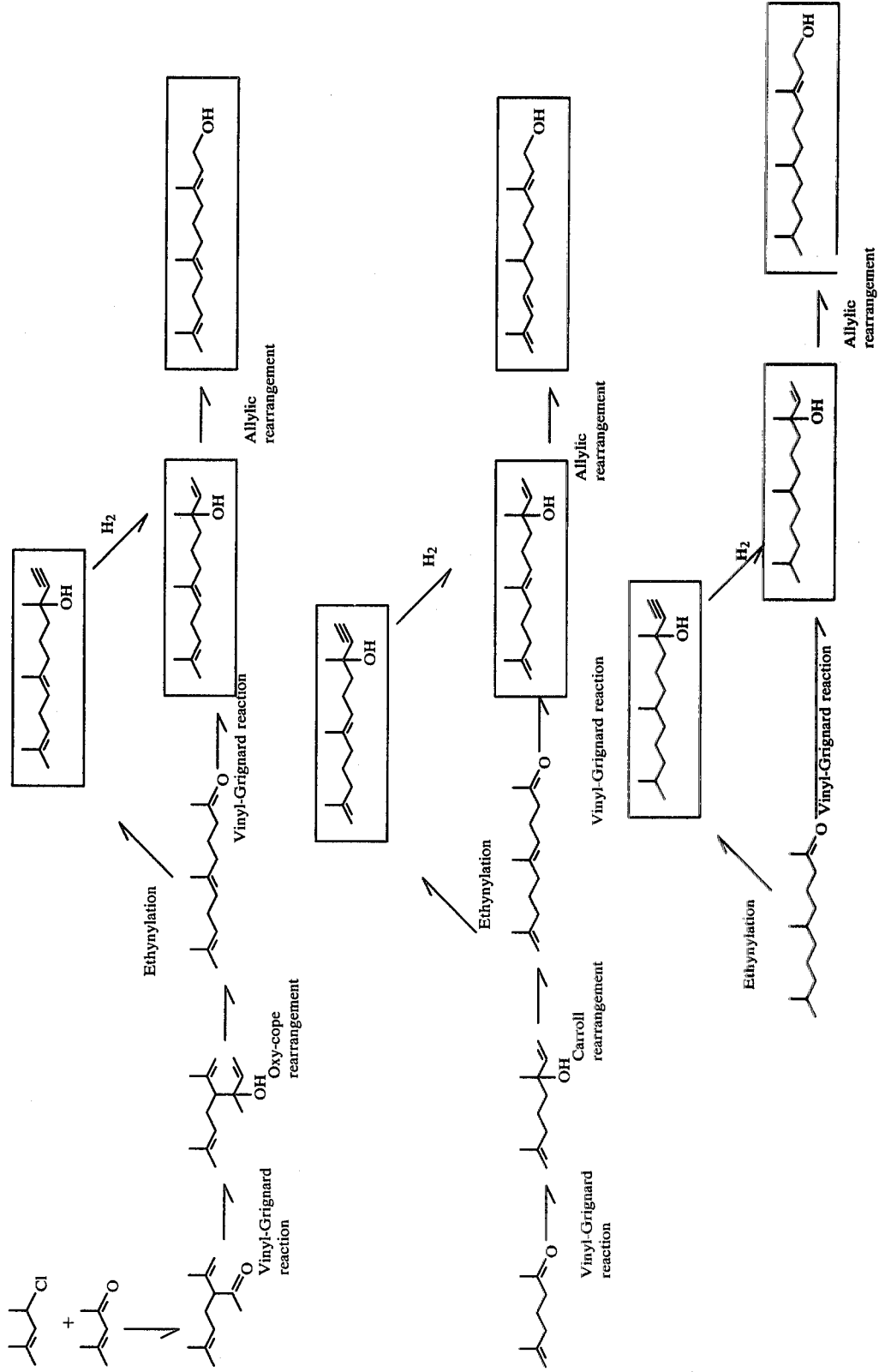

The organic carboxylic acid esters of the sesquiterpene alcohols of the present invention may be easily synthesized, for example, by the esterification of the corresponding sesquiterpene alcohol or reactive derivatives thereof with a desired organic carboxylic acid or a reactive derivative thereof, or by the transesterification reaction of any of the instant sesquiterpene alcohols with an organic carboxylic acid ester of a different alcohol.

The aquatic antifouling agent of this invention, displays extremely high activity against aquatic fouling organisms such as Hydrozoa, *Hydroides norvegica*, Ostrea, *Mytilus edulis, Balanus amphitrite*, Bryozoa, Ascidiacea, etc. at very low concentrations. For example, *Balanus amphitrite hawaiensis*, possesses a life cycle in which it undergoes, after fertilization, egg cleavage, the seven Nauplius stages, and the Cypris stage, where it acquires the ability to attach itself, before becoming an adult shellfish. At concentrations on the order of 0.1 to 25 ppm, the aquatic fouling agents of general formula (I) have sufficient activity to cause asphyxia or death to Balanus up through the Cypris stage. *Mytilus edulis* undergoes the stages of Trochofore, D-shaped larva, and Ambo before maturing into an adult shellfish. Similar concentrations of the sesquiterpene alcohols and carboxylic acid esters of formula (I) exhibit excellent activity against this shellfish up to the Ambo stage, a level of activity which is equivalent to the anti-attachment activity demonstrated against *Balanus amphitrite hawaiensis*.

The aquatic antifouling agents of general formula (I) are also able to inhibit the growth, and prevent and control the attachment of algae such as Ulva, Enteromorpha, Chlorella, Ectocarpus, and slime.

Moreover, because the sesquiterpene compounds of general formula (I) are decomposable by microorganisms, such as bacteria, etc., present in seawater at both their available and release concentrations, the antifouling agents of the instant invention are environmentally safe, and present a minimum possibility of accumulation in the tissues of aquatic organisms and animals.

The aquatic antifouling agents of the present invention, including mixtures thereof, may be dissolved directly in an aqueous environment to control aquatic fouling. Alternatively, the instant antifouling agents may be formulated into antifoulant compositions with suitable compatible carriers. The present invention thus provides, in a further embodiment, antifoulant compositions. As used herein, the term "compatible carrier" refers to any of the diluents; solvents; surface active agents; film-forming carriers such as oily varnishes, synthetic and natural resins, and paints; emulsions; solutions; and other vehicles well known to those skilled in the art from which antifoulant compositions are typically made. For example, the sesquiterpene compounds of general formula (I) may be prepared in the form of emulsifiable powders, wettable powders, emulsions, solutions, etc. containing one or more of the instant antifouling agents in combination with various diluents, and auxiliary additives such as solvents, surface active agents, etc. for addition to an aquatic body to control fouling. The instant antifouling agents, or mixtures thereof, may also be formulated into antifoulant coatings in combination with any of the well known film-forming vehicles such as paints, resins, varnishes etc. for application to an aquatic structure or structures exposed to aquatic environments.

Where seawater is utilized for industrial cooling purposes, fouling of heat exchanger conduits, water inlet and outlet conduits, and other waterways by aquatic fouling organisms can be completely controlled by dissolving or dispersing the instant aquatic antifouling agents at the rate of from about 0.001 to 50 ppm, preferably from about 0.05 to 50 ppm, in the seawater for a period of about 1 to 3 hours each day. For rendering ships' hulls, underwater structures, appliances, machinery, and so forth resistant to self-attaching organisms, the aquatic antifouling agents of the present invention may be deposited as such on the surface of the equipment to be protected in a suitable manner, formulated into an antifouling paint or coating composition with a film-forming carrier or vehicle and applied thereto. Generally, the film-forming vehicle may be an oily varnish, a synthetic resin, a synthetic rubber, a natural resin, or admixtures thereof with a comminuted pigment, hiding pigment, or the like. For example, the sesquiterpene compounds of general formula (I) may be employed as the active ingredient in the hydrophilic polymer antifouling coatings described in U.S. Pat. Nos. 3,575,123 and 3,990,381, herein incorporated by reference. When the aquatic antifouling agents of the present invention are utilized in an antifouling paint or coating composition, they will typically comprise from about 5 to 60 weight percent of the paint or coating composition.

For protecting fishnets or ropes, the instant aquatic antifouling agents, either alone or as formulated with a synthetic resin, solvent or other agent, may be compounded into the products, or applied as a coating thereto in admixture with a film-forming vehicle.

In order to more fully illustrate the inventive concepts of the present invention and the outstanding activity of the sesquiterpene compounds of formula (I) against aquatic fouling organisms, the following examples are presented which are intended to be merely illustrative and not limitative of the invention.

EXAMPLE 1

The antifouling activity of the instant compounds was compared with that of a large member of other compounds using *Artemia salina* L[*1] as test organism.

[*1] The testing procedure used in this example is known as the Artemia-scale method and is described in "New Methods of Screen Testing of Antifouling Toxicants and Coatings", Shizuo Mawatari, The Third International Congress For Conservation of Marine Materials, Gaithersburg, Maryland, U.S.A. (1973).

*Artemia salina* L tested:

A test population of Artemia larvae was prepared by filling a dish 19 cm across and 4 cm deep with sterile sea water to about one-half of its capacity and, then, placing therein dried *Artemia salina* L eggs. The eggs were then incubated in an incubator constantly illuminated with three 15 W fluorescent lights, and maintained with an inside temperature of 20° C. The larvae hatched after 48 hours of incubation and were separated from any unhatched eggs and transferred to a cylindrical glass vessel 9 cm across and 7 cm deep which was filled with sterile sea water to about one-half of its capacity. The hatched larvae were then incubated as above without food for 48 hours before being utilized in the antifoulant agent activity test.

Testing procedure:

Approximately 50 Artemia larvae, by rule of thumb, were pipetted into 50 ml glass containers filled with sterile sea water and containing a predetermined amount of one of the test compounds enumerated below. At a predetermined time after the start of the test, the response of the Artemia larvae to each test compound was evaluated. The response of the Artemia larvae to each compound was evaluated by classifying the larvae according to the following 4 conditions at a predetermined time after the start of the test by observation under a microscope, and then counting the number of larvae in each container exhibiting each condition:

Death: a larva that does not respond to pricking with a needle.

Half-death: A larva that barely responds to needle pricking or one which settles at the bottom of the container and breathes only with difficulty.

Weakened: A larva which retains the ability to move, but exhibits a slow and languid movement of the legs.

Healthy: The larva is able to move and continues to move vigorously.

After counting the number of larvae exhibiting each condition, a mortality factor was calculated for each test compound by multiplying the number of dead Artemia larvae by b 1, the number of half-deaths by 0.7, and the number of weakened larvae by 0.3, adding up the respective numbers, and expressing this sum as a percent based on the total number of the larvae involved in accordance with the following formula:

$$\text{Mortality} = 100 \times \frac{\text{No. of deaths} \times 1 + \text{No. of half-deaths} \times 0.7 + \text{No. of weakeneds} \times 0.3}{\text{Total number of larvae}}$$

The results of these comparative tests are summarized in Table 1, utilizing the following compounds as test compounds.

Unless otherwise noted, the farnesyl group, nerolidyl group, or dehydronerolidyl group in the compounds enumerated hereinbelow are not stereospecific.

Compound (1)

Farnesol (all trans)
A mixture farnesol of four stereo isomers.

Compound (1')
Compound (2)

Farnesyl acetate

Compound (3)

Farnesyl trimethylacetate

Compound (4)

Farnesyl β,β-dimethylacrylate

Compound (5)

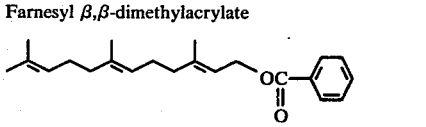
Farnesyl benzoate

Compound (6)

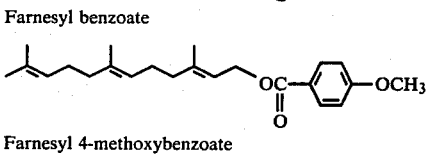
Farnesyl 4-methoxybenzoate

Compound (7)

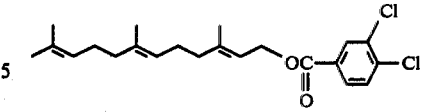
Farnesyl 3,4-dichlorobenzoate

Compound (8)

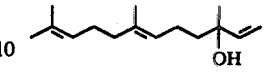
Nerolidol

Compound (9)

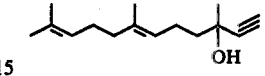
Dehydro nerolidol

Compound (10)

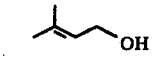
Prenol

Compound (11)

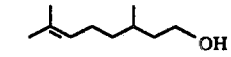
Citronellol

Compound (12)

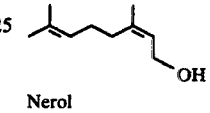
Nerol

Compound (13)

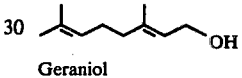
Geraniol

Compound (14)

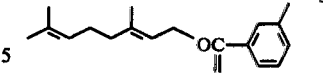
Geranyl 3-methylbenzoate

Compound (15)

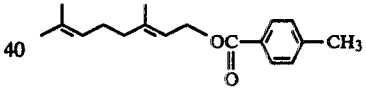
Geranyl 4-methylbenzoate

Compound (16)

Hexahydro farnesol

Compound (17)

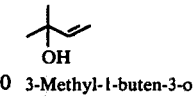
3-Methyl-1-buten-3-ol

Compound (18)

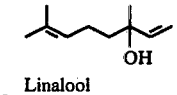
Linalool

Compound (19)

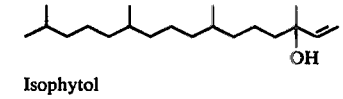
Isophytol

Compound (20)

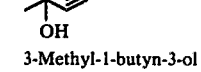
3-Methyl-1-butyn-3-ol

Compound (21)

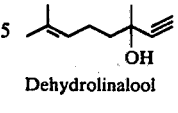
Dehydrolinalool

Table 1

| Test Compound | Concentration of test compound (ppm) | % Mortality After 1 hr. | After 2 hrs. | After 4 hrs. | After 6 hrs. | After 24 hrs. |
|---|---|---|---|---|---|---|
| Compound (1) | 1.6 | 9.6 | 21.7 | 18.3 | 20.7 | 63.0 |
| | 3.1 | 28.2 | 35.2 | 41.6 | 51.6 | 96.4 |
| | 6.2 | 30.7 | 38.7 | 47.7 | 60.1 | 100 |
| | 12.5 | 31.0 | 39.9 | 45.2 | 61.2 | 100 |
| | 25 | 35.4 | 48.2 | 68.1 | 76.6 | 100 |
| | 50 | 45.3 | 53.6 | 68.5 | 78.9 | 100 |
| | 100 | 50.9 | 59.6 | 74.8 | 84.4 | 100 |
| Compound (1') | 6.25 | 30.8 | 57.6 | 78.2 | 100 | 100 |
| | 12.5 | 69.2 | 70.0 | 100 | 100 | 100 |
| | 25 | 70.0 | 100 | 100 | 100 | 100 |
| | 50 | 70.0 | 100 | 100 | 100 | 100 |
| | 100 | 70.0 | 100 | 100 | 100 | 100 |
| Compound (2) | 50 | 30.0 | 30.0 | 30.0 | 30.0 | 100 |
| | 100 | 30.0 | 30.0 | 30.0 | 30.0 | 100 |
| Compound (3) | 50 | 0 | 0 | 30.0 | 30.0 | 100 |
| | 100 | 30.0 | 30.0 | 30.0 | 70.0 | 100 |
| Compound (4) | 50 | 0 | 0 | 17.2 | 30.0 | 30.0 |
| | 100 | 30.0 | 30.0 | 30.0 | 70.0 | 100 |
| Compound (5) | 25.5 | 30.0 | 30.0 | 30.0 | 37.6 | 100 |
| | 50 | 30.0 | 30.0 | 30.0 | 53.2 | 100 |
| | 100 | 30.0 | 30.0 | 50.4 | 70.0 | 100 |
| Compound (6) | 12.5 | 0 | 0 | 43.4 | 46.4 | 51.1 |
| | 25 | 0 | 30.0 | 45.2 | 51.4 | 71.0 |
| | 50 | 30.0 | 30.0 | 30.0 | 56.2 | 100 |
| | 100 | 30.0 | 30.0 | 70.0 | 70.0 | 100 |
| Compound (7) | 50 | 30.0 | 30.0 | 30.0 | 31.6 | 100 |
| | 100 | 30.0 | 30.0 | 32.4 | 70.0 | 100 |
| Compound (8) | 12.5 | 0.9 | 2.9 | 14.8 | 20.7 | 27.9 |
| | 25 | 5.9 | 14.7 | 40.2 | 50.2 | 93.6 |
| | 50 | 15.3 | 28.7 | 58.1 | 82.0 | 100 |
| | 100 | 29.0 | 43.1 | 66.3 | 80.4 | 100 |
| Compound (9) | 12.5 | 4.9 | 15.5 | 32.4 | 44.1 | 62.2 |
| | 25 | 7.6 | 33.1 | 50.7 | 62.7 | 98.5 |
| | 50 | 29.4 | 47.7 | 72.6 | 91.5 | 100 |
| | 100 | 33.8 | 66.4 | 77.0 | 98.1 | 100 |
| Compound (10) | 62.5 | 0 | 0 | 0 | 0 | 0 |
| | 125 | 0 | 0.3 | 0.8 | 0.8 | 1.4 |
| | 250 | 3.4 | 4.5 | 2.0 | 0.3 | 7.1 |
| Compound (11) | 50 | 1.0 | 3.3 | 5.9 | 7.2 | 7.1 |
| | 100 | 32.8 | 52.6 | 74.6 | 83.2 | 51.6 |
| Compound (12) | 50 | 0 | 0 | 0.3 | 0.3 | 7.7 |
| | 100 | 0.4 | 0.7 | 1.7 | 3.9 | 38.4 |
| Compound (13) | 50 | 1.1 | 3.0 | 4.5 | 3.3 | 19.8 |
| | 100 | 29.6 | 34.4 | 42.2 | 51.1 | 74.7 |
| Compound (14) | 12.5 | 0 | 0.4 | 1.7 | 2.1 | 30.3 |
| | 25 | 0 | 0.8 | 1.8 | 2.2 | 32.2 |
| | 50 | 0 | 0 | 0.2 | 0.5 | 39.0 |
| | 100 | 0 | 1.4 | 3.4 | 4.3 | 40.0 |
| Compound (15) | 12.5 | 0 | 0 | 0.3 | 0.8 | 49.3 |
| | 25 | 0 | 0.3 | 0.8 | 1.9 | 44.4 |
| | 50 | 0 | 0.2 | 0.9 | 2.2 | 52.3 |
| | 100 | 0.6 | 0.4 | 0.9 | 2.3 | 50.8 |
| Compound (16) | 50 | 0 | 0 | 0 | 0 | 0 |
| | 100 | 0 | 12.0 | 0 | 0 | 0 |
| Compound (17) | 125 | 0 | 0 | 0 | 0 | 0 |
| | 250 | 0.3 | 0.5 | 0.2 | 0 | 0 |
| Compound (18) | 62.5 | 0 | 0 | 0 | 0 | 2.0 |
| | 125 | 1.2 | 2.1 | 2.1 | 0.3 | 7.5 |
| | 250 | 35.2 | 49.4 | 66.2 | 57.1 | 49.6 |
| Compound (19) | 25 | 0 | 0 | 0 | 0.2 | 33.5 |
| | 50 | 0.3 | 0.3 | 1.7 | 2.0 | 37.4 |
| | 100 | 0.2 | 0.4 | 1.1 | 1.1 | 39.9 |
| Compound (20) | 125 | 0 | 0 | 0 | 0 | 0 |
| | 250 | 0.5 | 0.4 | 0 | 0 | 0 |
| Compound (21) | 62.5 | 0 | 0 | 0 | 0 | 0 |
| | 125 | 0 | 0 | 0.5 | 0.9 | 1.9 |
| | 250 | 5.5 | 14.6 | 18.2 | 18.8 | 33.1 |

The foregoing comparative tests clearly establish that the sequiterpene compounds of formula (I) exhibit outstanding activity against aquatic fouling organisms, an activity superior to conventional antifouling agents such as geraniol. Accordingly, the sesquiterpene compounds of formula (I) constitute highly efficacious antifailing agents, exhibiting a heretofore unobtainable efficacy against aquatic failing organisms.

EXAMPLE 2

Antifoulant paint compositions were prepared by admixing No. 1 bottom point (a commercial product) with 15 weight % of one of the sesquiterpene compounds of formula (I) as antifoulant agent. Cold-finished steel plates 100×100×3 mm, coated once with a wash primer and twice with No. 1 bottom point, then received a final coating with an antifoulant paint containing one of the test compounds (1), (1'), (2) to (9) and (22) to (28) as the antifoulant agent. The test compounds (22) to (28) are as follows:

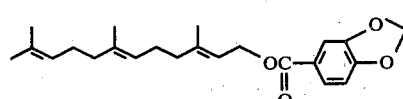

Compound (22)

Farnesyl 3,4-methylenedioxybenzoate

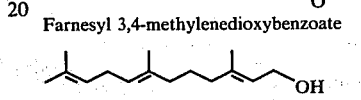

Compound (23)

3,7,11-Trimethyl-2,7,10-dodecatrien-1-ol

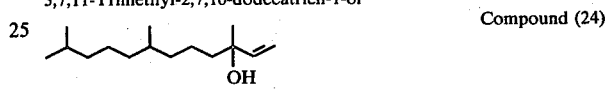

Compound (24)

3,7,11-Trimethyl-1-dodecen-3-ol

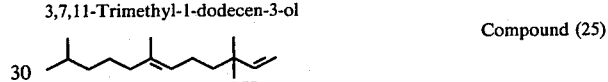

Compound (25)

3,7,11-Trimethyl-1,6-dodecadien-3-ol

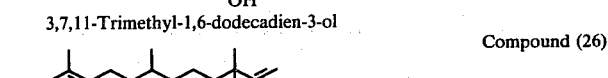

Compound (26)

3,7,11-Trimethyl-1,10-dodecadien-3-ol

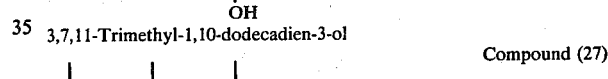

Compound (27)

Nerolidyl acetate

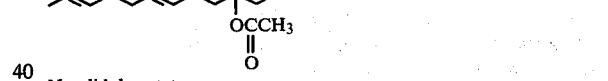

Compound (28)

Dehydro nerolidyl acetate

Each test plate was then suspended in sea water at a depth of 15 meters from a raft on the water surface and evaluated for fouling. After immersion for three months, each plate, without exception, having a coating of an antifoulant paint containing as active ingredient, one of the aforementioned test compounds was found to have substantially no deposits of aquatic fouling organisms thereon.

EXAMPLE 3

20% of each of compounds (1), (2), (5), (7), (8) and (9) was admixed with 15% of the nonionic-anionic mixture of surface active agents marketed under the tradename "Sorpol" by Toho Kagaku Kogyo K. K., and 65% of xylene to prepare an emulsion.

Using six heat exchanger waterways [*2] of the single-pass type in which sea water was utilized as the heat exchange medium, the antifouling activity of each of the above emulsions was evaluated during three winter months. The flow rate in each waterway was 100 m³/hr. One of the above aquatic antifouling agents was introduced into each waterway by first diluting 0.1 kg of each of the above emulsions with 1 m³ of sea water and pouring the entire admixture into the waterway over a period of one hour. The above operation was performed six times daily for a period of three months. The concentration of each of the above mixtures in the waterway (at the time of addition of each emulsion) was 0.5 ppm (0.1 ppm of active ingredient). As controls, chlorine gas treated and untreated waterways were provided. The concentration of chlorine in the chlorine control waterway was maintained at 1 ppm throughout the testing period. Fouling in each waterway was evaluated by visually inspecting a slate panel provided on a centrally located wall of each waterway for the attachment of young shellfish and algae.

(*2) The waterway is made of concrete and exposed to the air, and one end of the waterway is connected to the heat exchanger conduit and the other end drains into the sea.

The results are set forth in Table 2.

Table 2

| Test compound | No. of young shellfish (per m²) | Algae |
| --- | --- | --- |
| Compound | | |
| (1) | 0 | Not attached |
| (2) | 0 | Not attached |
| (5) | 0 | Not attached |
| (7) | 0 | Not attached |
| (8) | 2 | Not attached |
| (9) | 1 | Not attached |
| Chlorine gas control | 380 | Sparse |
| Untreated control | 957 | Abundant |

The young shellfish attached to each panel were found to be mainly *Mytilus edulis.*

EXAMPLE 4

Activity against fresh water chlorella

A series of five solutions containing fresh water chlorella (*Chlorella ellipsoidea*) and different concentrations of farnesol were prepared by pipeting 5 ml of a cultural medium suitable for the growth of fresh water chlorella, 50 ml of different farnesol stock solutions, and 5 ml of fresh water chlorella stock culture into a small-sized flat flask to make a total of 60 ml. The composition of the fresh water chlorella cultural medium was as follows:

| 4N—KNO₃ | 5.0g | FeSO₄ . 7H₂O | 0.003g |
| --- | --- | --- | --- |
| KH₂PO₄ | 1.25g | Water | 1000 ml |
| Mg₂SO₄ . 7H₂O | 2.5g | | |

The amount of growth of fresh water chlorella in each of these solutions was then evaluated on the first, 2nd, 4th and 6th days after the start of the experiment.

Determination of the amount of growth of fresh water chlorella in each solution was as follows:

A 5 ml sample of each of the above solutions was pipetted into a heamatocrit. The chlorella cells were then forced into the constricted portion of the heamatocrit by centrifugation at 4,000 r.p.m. for 20 minutes. The volume of Chlorella cells present in each solution on each day was obtained by reading a calibrated scale on the heamatocrit. This data was then expressed as a function of time to provide a measure of the rate of growth over time.

Table 3

| Concentration (ppm) | Change in growth rate with time | | | |
| --- | --- | --- | --- | --- |
| | 1st day | 2nd day | 4th day | 6th day |
| Control | 0.4 | 2.0 | 5.0 | 10.5 |
| 1 | 0.4 | 2.0 | 5.4 | 10.5 |
| 10 | 0.5 | 1.1 | 2.0 | 5.5 |
| 100 | 0.5 | 1.0 | 1.0 | 1.1 |
| 1000 | 0.6 | 0.7 | 0.7 | 0 |

Table 4

| Concentration (ppm) | Change in relative growth rate with time | | | |
| --- | --- | --- | --- | --- |
| | 1st day | 2nd day | 4th day | 6th day |
| Control | 3.8 | 19.0 | 47.6 | 100 |
| 1 | 3.8 | 19.0 | 51.4 | 100 |
| 10 | 4.8 | 10.5 | 19.0 | 52.4 |
| 100 | 4.8 | 9.5 | 9.5 | 10.5 |
| 1000 | 5.7 | 6.7 | 6.7 | 0 |

It is thus seen from the foregoing examples that the sesquiterpene compounds of formula (I), and particularly farnesol and its carboxylic acid esters, exhibit outstanding antifouling activity, and provide long-term protection against fouling by aquatic fouling organisms. Accordingly, the present invention provides a significant advance in the art of controlling aquatic fouling organisms.

While the instant invention has been described in terms of various preferred embodiments, and illustrated by numerous examples, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A method for rendering structures exposed to an aqueous environment resistant to fouling by barnacles, algae, bryozoa, slime, hydrozoa, mussels, oysters, and ascidiacea organisms in said environment, comprising contacting said structures with an effective antifouling amount of a sesquiterpene compound of the general formula (I):

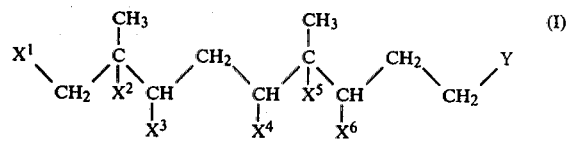

wherein $X^1$, $X^2$ and $X^3$ each is a hydrogen atom, or one of $X^1$ and $X^3$ is a hydrogen atom with the other and $X^2$ representing a double bond in the carbon chain of the compound; $X^4$, $X^5$ and $X^6$ each is a hydrogen atom, or one of $X^4$ and $X^6$ is a hydrogen atom with the other and $X^5$ representing a double bond in the carbon chain of the compound; and Y is a group selected from the group consisting of:

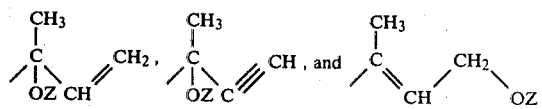

wherein Z is a hydrogen atom or

where R is a hydrogen atom or a hydrocarbon group which may optionally be substituted; or mixtures thereof.

2. The method of claim 1, wherein said structures are rendered resistant to fouling by adding an effective antifouling amount of said sesquiterpene compound of formula (I) to said aqueous environment.

3. The method of claim 2, wherein said sesquiterpene compound of formula (I) is added to said aqueous environment at a rate of about 0.001 to about 50 ppm for a period of about 1 to about 3 hours each day.

4. The method of claim 2, wherein said sesquiterpene compound of formula (I) is added to said aqueous environment at a rate of about 0.05 to 50 ppm for a period of about 1 to about 3 hours each day.

5. The method of claim 2, wherein said sesquiterpene compound of formula (I) is prepared as an emulsion and added to said aqueous environment.

6. The method of claim 1, wherein said sesquiterpene compound is formulated into an antifoulant coating with a suitable film-forming carrier and applied to said structure.

7. The method of claim 6, wherein said film-forming carrier is selected from the group consisting of oily varnishes, synthetic rubbers, natural resins, and admixtures thereof with a pigment.

8. The method of claim 6, wherein said sesquiterpene compound of formula (I) comprises about 5 to about 60% by weight of said antifoulant coating.

9. The method of claim 1, wherein said sesquiterpene compound of formula (I) is compounded into said structures.

10. The method of claim 9, wherein said sesquiterpene compound is formulated with a compatible carrier selected from the group consisting of synthetic resins and solvents and compounded into said structures.

11. The method of claim 1, wherein R in the sesquiterpene compound of formula (I) is a hydrocarbon group selected from the group consisting of alkyl groups of 1 to 8 carbon atoms, alkenyl groups of 2 to 8 carbon atoms, aralkyl groups of 7 to 11 carbon atoms, and aryl groups of 6 to 10 carbon atoms.

12. The method of claim 11, wherein R is a hydrocarbon group substituted with a group selected from the group consisting of halogen, alkyl, hydroxy, alkoxy, nitro, dioxy, and amino groups.

13. The method of claim 12, wherein R is a hydrocarbon group selected from the group consisting of methyl, ethyl, propyl, butyl, pentyl, ethenyl, propenyl, butenyl, benzyl, piperonyl, methylbenzyl, phenyl, hydroxyphenyl, 3,4-methylenedioxyphenyl, chlorophenyl, dichlorophenyl, methylphenyl, methylaminophenyl, methoxyphenyl and nitrophenyl.

14. The method of claim 1, wherein Y is the sesquiterpene compound of formula (I) is a group of the formula:

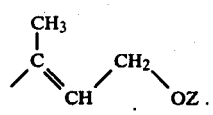

15. The method of claim 14, wherein Z is a hydrogen atom.

16. The method of claim 14, wherein said sesquiterpene compound is a compound of the general formula (2):

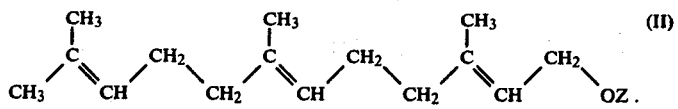

17. The method of claim 16, wherein said sesquiterpene compound of formula (II) is farnesol.

18. The method of claim 16, wherein Z in the sesquiterpene compound of general formula (II) is

19. The method of claim 18, wherein R is selected from the group consisting of alkyl groups of 1 to 8 carbon atoms, alkenyl groups of 2 to 8 carbon atoms, substituted and unsubstituted aralkyl groups of 7 to 11 carbon atoms, and substituted and unsubstituted aryl groups of 6 to 10 carbon atoms.

20. The method of claim 19, wherein R is selected from the group consisting of lower alkyl groups, lower alkenyl groups, a phenyl group, or a phenyl group substituted by lower alkyl, lower alkoxy, chlorine or dioxy groups.

21. The method of claim 20, wherein said sesquiterpene compound is selected from the group consisting of farnesyl 3,4-methylenedioxybenzoate, farnesyl acetate, farnesyl trimethylacetate, farnesyl β,β-dimethyl acrylate, farnesyl benzoate, farnesyl 4-methoxybenzoate, and farnesyl 3,4-dichlorobenzoate.

22. The method of claim 1, wherein Y in the sesquiterpene compound of general formula (I) is a group of the formula:

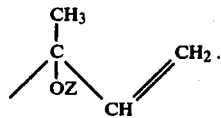

23. The method of claim 22, wherein Z is a hydrogen atom.

24. The method of claim 22, wherein said sesquiterpene compound is a compound of the general formula (III):

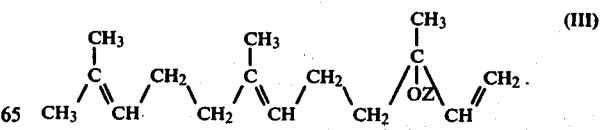

25. The method of claim 24, wherein said sesquiterpene compound of general formula (III) is nerolidol.

26. The method of claim 24, wherein Z in the compound of formula (III) is

27. The method of claim 26, wherein R is selected from the group consisting of alkyl groups of 1 to 8 carbon atoms, alkenyl groups of 2 to 8 carbon atoms, substituted and unsubstituted aralkyl groups of 7 to 11 carbon atoms, and substituted and unsubstituted aryl groups of 6 to 10 carbon atoms.

28. The method of claim 27, wherein R is selected from the group consisting of lower alkyl groups, lower alkenyl groups, a phenyl group, or a phenyl group substituted by lower alkyl, lower alkoxy, chlorine or dioxy groups.

29. The method of claim 28, wherein said sesquiterpene compound is nerolidyl acetate.

30. The method of claim 1, wherein Y in the general formula (I) is

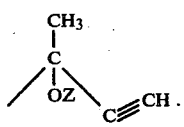

31. The method of claim 30, wherein Z is a hydrogen atom.

32. The method of claim 30, wherein said sesquiterpene compound is a compound of the general formula (IV):

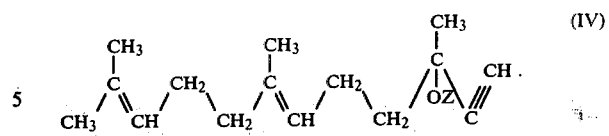

33. The method of claim 32, wherein said sesquiterpene compound of formula (IV) is dehydronerolidol.

34. The method of claim 32, wherein Z in the sesquiterpene compound of formula IV is

35. The method of claim 34, wherein R is selected from the group consisting of alkyl groups of 1 to 8 carbon atoms, alkenyl groups of 2 to 8 carbon atoms, substituted and unsubstituted aralkyl groups of 7 to 11 carbon atoms, and substituted and unsubstituted aryl groups of 6 to 10 carbon atoms.

36. The method of claim 35, wherein R is selected from the group consisting of lower alkyl groups, lower alkenyl groups, a phenyl group, or a phenyl group substituted by lower alkyl, lower alkoxy, chlorine or dioxy groups.

37. The method of claim 36, wherein said sesquiterpene compound is dehydronerolidyl acetate.

38. The method of claim 1, wherein the sesquiterpene compound (I) is an ester.

39. The method of claim 1, wherein R is the residue of an acid selected from the group consisting of formic acid, acetic acid, propionic acid, butyric acid, valeric acid, pivalic acid, acrylic acid, methacrylic acid, crotonic acid, senecioic acid (β,β-dimethylacrylic acid), benzoic acid, p-hydroxybenzoic acid, p-chlorobenzoic acid, 3,4-dichlorobenzoic acid, p-methylbenzoic acid, o-methylaminobenzoic acid, p-methoxybenzoic acid, piperonylic acid and p-nitrobenzoic acid.

* * * * *